(12) United States Patent
Gunnarssonn et al.

(10) Patent No.: US 9,907,676 B2
(45) Date of Patent: Mar. 6, 2018

(54) PROSTHETIC FOOT WITH HYBRID LAYUP (71) Applicant: Össur hf, Reykjavík (IS)

(72) Inventors: Ragnar Orn Gunnarssonn, Reykjavík (IS); Christophe G. Lecomte, Reykjavík (IS); Benedikt Skulason, Reykjavík (IS)

(73) Assignee: Össur hf, Reykjavik (IS)

( * ) Notice: Subject to any disclaimer, the term of this patent is extended or adjusted under 35 U.S.C. 154(b) by 347 days.

(21) Appl. No.: 14/737,219

(22) Filed: Jun. 11, 2015

(65) Prior Publication Data

US 2016/0000582 A1    Jan. 7, 2016

Related U.S. Application Data

(63) Continuation of application No. 13/804,896, filed on Mar. 14, 2013, now abandoned.
(Continued)

(51) Int. Cl.
*B32B 41/00* (2006.01)
*A61F 2/50* (2006.01)
*A61F 2/66* (2006.01)

(52) U.S. Cl.
CPC .............. *A61F 2/5044* (2013.01); *A61F 2/66* (2013.01); *A61F 2002/503* (2013.01);
(Continued)

(58) Field of Classification Search
CPC .... A61F 2/5044; A61F 2/66; A61F 2002/503; A61F 2002/5055; A61F 2002/5056; A61F 2002/6657
(Continued)

(56) References Cited

U.S. PATENT DOCUMENTS

| 4,397,048 A | 8/1983 | Brown et al. |
| 4,547,913 A | 10/1985 | Phillips |

(Continued)

FOREIGN PATENT DOCUMENTS

| WO | WO 93/04645 A1 | 3/1993 |
| WO | WO 2014/008306 | 3/2014 |

OTHER PUBLICATIONS

International Search Report and Written Opinion in PCT Application No. PCT/US13/49156, dated Nov. 26, 2013.
(Continued)

*Primary Examiner* — Michael N Orlando
*Assistant Examiner* — Joshel Rivera
(74) *Attorney, Agent, or Firm* — Knobbe Martens Olson & Bear LLP (57) ABSTRACT

A prosthetic foot has a plate-like foot member with a core section substantially defined by one or more layers comprising a first material fiber, an upper section disposed above the core section, the upper section substantially defined by one or more layers comprising a second material fiber, and a lower section disposed below the core section, the lower section substantially defined by one or more layers comprising a third material fiber, where the upper, lower and core sections together define a total thickness of the plate-like elongate foot member. An idealized ratio of the cross sectional area of each section can be determined such that under an applied load provided to the hybrid layup, the ratio of maximum stress of a given section over the flexural strength of that given section is approximately equal for all sections of the hybrid layup. The hybrid layup arrangement can be configured to have a greater strength, but generally the same stiffness, as a similar foot member made of carbon fiber.

19 Claims, 5 Drawing Sheets

Related U.S. Application Data (60) Provisional application No. 61/668,885, filed on Jul. 6, 2012.

(52) U.S. Cl.
CPC ............... *A61F 2002/5055* (2013.01); *A61F 2002/5056* (2013.01); *A61F 2002/6657* (2013.01)

(58) Field of Classification Search
USPC ..................... 156/64, 350, 351, 378, 379
See application file for complete search history.

(56) References Cited

U.S. PATENT DOCUMENTS

| | | | |
|---|---|---|---|
| 4,688,338 A | 8/1987 | Brown | |
| 4,959,073 A | 9/1990 | Merlette | |
| 5,037,444 A | 8/1991 | Phillips | |
| 5,156,631 A | 10/1992 | Merlette | |
| 5,312,669 A | 5/1994 | Bedard | |
| 5,406,723 A | 4/1995 | Okajima | |
| 5,538,271 A | 7/1996 | Abondance | |
| 5,725,598 A | 3/1998 | Phillips | |
| 5,766,724 A | 6/1998 | Tailor et al. | |
| 6,416,843 B1 | 7/2002 | Rata et al. | |
| 7,128,960 B2 | 10/2006 | Walz et al. | |
| 7,347,877 B2 | 3/2008 | Clausen et al. | |
| 7,618,463 B2 | 11/2009 | Oddsson et al. | |
| 7,846,000 B2 | 12/2010 | Cox | |
| 7,846,213 B2 | 12/2010 | Lecomte et al. | |
| 7,879,110 B2 | 2/2011 | Phillips | |
| 7,998,221 B2 | 8/2011 | Lecomte et al. | |
| 8,007,544 B2 | 8/2011 | Jonsson et al. | |
| 8,025,699 B2 | 9/2011 | Lecomte et al. | |
| 8,128,709 B2 | 3/2012 | Thorhallsdottir et al. | |
| 8,377,146 B2 | 2/2013 | Jonsson et al. | |
| 8,685,109 B2 | 4/2014 | Clausen et al. | |
| 8,858,649 B2 | 10/2014 | Jonsson et al. | |
| 2004/0213952 A1 | 10/2004 | Takemura et al. | |
| 2006/0212131 A1 | 9/2006 | Curtis | |
| 2007/0027557 A1 | 2/2007 | Jonsson et al. | |
| 2007/0100465 A1 | 5/2007 | Egan | |
| 2010/0042228 A1 | 2/2010 | Doddroe et al. | |
| 2012/0010730 A1 | 1/2012 | Lecomte et al. | |
| 2012/0165958 A1 | 6/2012 | Clausen et al. | |
| 2012/0180343 A1 | 7/2012 | Auger et al. | |
| 2013/0144403 A1 | 6/2013 | Lecomte et al. | |
| 2013/0173023 A1 | 7/2013 | Lecomte et al. | |
| 2014/0257523 A1 | 9/2014 | Clausen et al. | |

OTHER PUBLICATIONS

MacKenzie, Craig, "Laminations and Carbon Fiber", http://www.oandp.com/articles/2008-03_15.asp, Mar. 15, 2008, pp. 3.

"Renegade® A-T", Freedom Innovations, Brochure http://www.freedom-innovations.com/assets/pdf/RenegadeATBroFinal.pdf, Sep. 2011, pp. 6.

Extended European Search Report and Written Opinion in EP Application No. 13812799.8, dated Apr. 4, 2016.

Office Action in European Application No. 13 812 799.8, dated Mar. 21, 2017.

H. Fukunaga et al.: "On Laminate Configurations for Simultaneous Failure", Journal of Composite Materials, vol. 22, No. 3, Jan. 1, 1988, pp. 271-286.

N G R Iyengar: "Optimization in Structural design", Sep. 2004, XP055354445, Available as of Apr. 19, 2017, at http://www.iitk.ac.in/directions/directsept04/Iyenger-new.pdf.

R H Lopez et al.: "Optimisation of Laminated Composite Plates Considering Different Failure Criteria", Jul. 28, 2009, XP055354429, Available as of Apr. 19, 2017, at http://iccm-central.org/Proceedings/ICCM17proceedings/Themes/Behaviour/STRUCTURALANALY&OPTIM/INT-STRUCTANALYSIS&OPTIM/IF22.8Luersen.pdf.

PROSTHETIC FOOT WITH HYBRID LAYUP

INCORPORATION BY REFERENCE TO ANY PRIORITY APPLICATIONS

Any and all applications, for which a foreign or domestic priority claim is identified in the Application Data Sheet as filed with the present application, are hereby incorporated by reference. This application is a continuation of U.S. patent application Ser. No. 13/804,896, filed on Mar. 14, 2013, entitled "PROSTHETIC FOOT WITH HYBRID LAYUP," which claims the benefit of priority under 35 U.S.C. § 119(e) of U.S. Provisional Application No. 61/668,885, filed on Jul. 6, 2012, the entire disclosure of each of which is incorporated herein by reference.

BACKGROUND

Field of the Invention

The present application is directed to prosthetic feet, and more particularly to prosthetic feet having a hybrid material layup arrangement.

Description of the Related Art

Various types of prosthetic foot devices are available as substitutes for human feet. Conventional prosthetic feet, which can be made of various layers of carbon fiber, are generally provided in a number of sizes and categories (e.g., activity categories) to fit the different population of users and activity levels of the users. For example, users who engage in low impact activities such as walking and gardening may need a prosthetic foot with a particular stiffness and/or strength. Users who engage in high impact activities, such as running or playing sports, however, may need the prosthetic foot to have a higher strength and/or different stiffness than that of a low activity user. In a conventional prosthetic foot, designing the prosthetic foot for an increase in strength requires an increase in the overall thickness of the prosthetic foot and results in a corresponding increase in stiffness (i.e., a decrease in flexibility or flexion of the prosthetic foot). The increase in stiffness and thickness adds to the weight of the foot and may require a user to exert more force on the foot during ambulation.

SUMMARY

In view of the foregoing, there is a need for an improved prosthetic foot that can provide the same flexibility or stiffness as a similarly sized conventional prosthetic foot, while providing an increase in strength over the similarly sized conventional prosthetic foot. Additionally, there is a need for an improved prosthetic foot that can provide the same strength as a similarly sized conventional prosthetic foot, while providing an increase in flexibility over the similarly sized conventional prosthetic foot. Such improved prosthetic feet would be able to provide the enhanced strength or flexibility with a limited and/or minimal increase in overall thickness and/or weight as compared to the similarly sized conventional prosthetic feet.

In accordance with one embodiment, a prosthetic foot is provided. The prosthetic foot comprises a core section and one or more layers disposed on a top and bottom side of the core section so that the core section is interposed between the outer layers. The core section has one or more carbon fiber layers. The one or more outer layers have glass fiber layers.

In accordance with one embodiment, a prosthetic foot is provided. The prosthetic foot comprises at least a first section and a second section provided on top of one another. The first section is substantially defined by one or more layers comprising a first fiber material and the second section is substantially defined by one or more layers comprising a second fiber material. The sections together define a composite member and further define the total thickness of the plate-like elongate foot member. The thickness of each section relative to the total thickness of the composite member is configured such that the ratio of maximum stress of a given section over the flexural strength of that given section is approximately equal for all sections, wherein the maximum stress of a given section is the maximum stress experienced by that section under an applied load provided to the composite member.

In accordance with one embodiment, a prosthetic foot is provided. The prosthetic foot comprises a plate-like elongate foot member that comprises a core section substantially defined by one or more layers comprising a first material fiber. The foot member also comprises an upper section disposed above the core section, the upper section substantially defined by one or more layers comprising a second material fiber. The foot member also comprises a lower section disposed below the core section, the lower section substantially defined by one or more layers comprising a third material fiber, where the upper, lower and core sections together define a total thickness of the plate-like elongate foot member. The upper, lower and core sections are configured so as to fail substantially simultaneously when the plate-like member is subjected to a bending force greater than a flexural breaking force of the plate-like foot member.

In accordance with one embodiment, a prosthetic foot is provided. The prosthetic foot comprises at least a first section and a second section provided on top of one another. The first section is substantially defined by one or more layers comprising a first fiber material and the second section is substantially defined by one or more layers comprising a second fiber material. The sections together define a composite member and further define the total thickness of the plate-like elongate foot member. The overall strength of the composite member is greater than the strength of a hypothetical single-section plate-like foot member sized to have approximately the same stiffness as the composite member, wherein the hypothetical single-section plate-like foot member is made entirely of only one or more layers comprising either the first fiber material or the second fiber material.

In accordance with one embodiment, a prosthetic foot is provided. The prosthetic foot comprises at least a first section and a second section provided on top of one another. The first section is substantially defined by one or more layers comprising a first fiber material and the second section is substantially defined by one or more layers comprising a second fiber material. The sections together define a composite member and further define the total thickness of the plate-like elongate foot member. The overall flexibility of the composite member is greater than the flexibility of a hypothetical single-section plate-like foot member sized to have approximately the same strength as the composite member, wherein the hypothetical single-section plate-like foot member is made entirely of only one or more layers comprising either the first fiber material or the second fiber material.

In accordance with one embodiment, a prosthetic foot is provided. The prosthetic foot comprises a plate-like elongate foot member that comprises a core section substantially defined by one or more layers comprising a first material fiber. The foot member also comprises an upper section disposed above the core section, the upper section substantially defined by one or more layers comprising a second material fiber. The foot member also comprises a lower section disposed below the core section, the lower section substantially defined by one or more layers comprising a third material fiber, where the upper, lower and core sections together define a total thickness of the plate-like elongate foot member. The core section is configured to fail when the plate-like member is subjected to a bending force greater than a flexural breaking force of the plate-like foot member. The core section configured to break and the upper and lower sections configured to remain intact and contain the broken core section to maintain the plate-like foot member as one piece.

DETAILED DESCRIPTION

Embodiments of the invention will now be described with reference to the accompanying figures, wherein like numerals refer to like elements throughout. Although several embodiments, examples and illustrations are disclosed below, it will be understood by those of ordinary skill in the art that the invention described herein extends beyond the specifically disclosed embodiments, examples and illustrations and can include other uses of the invention and obvious modifications and equivalents thereof. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

Figure 1:
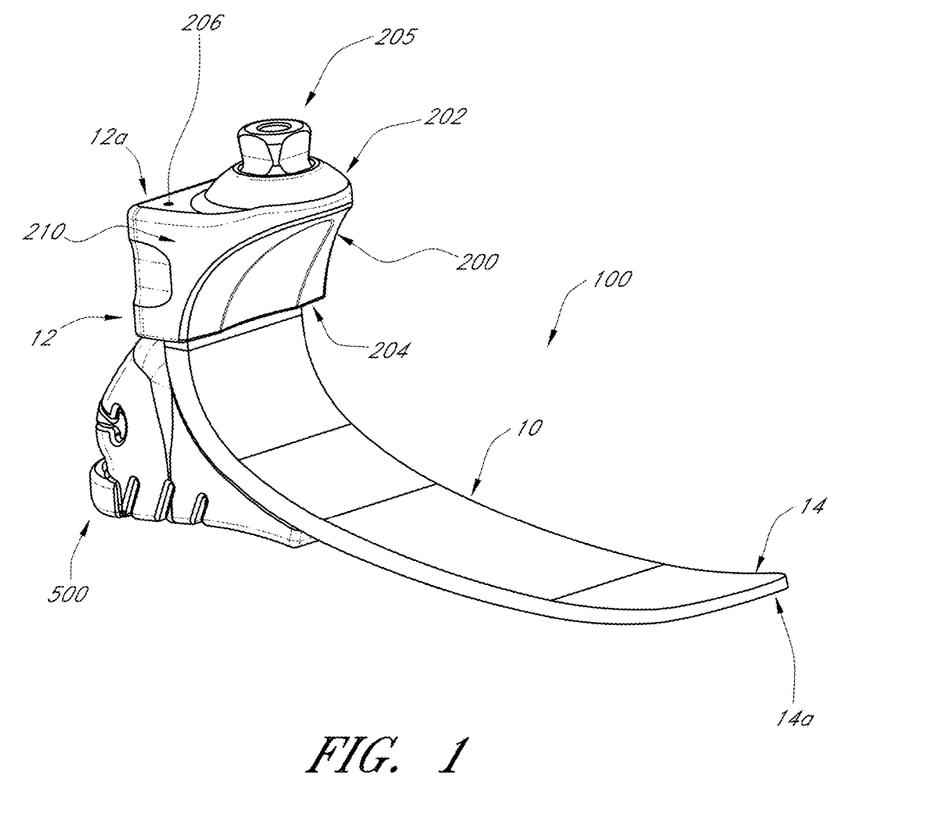
FIG. 1 is a perspective schematic view of one embodiment of a prosthetic foot.

FIG. 1 illustrates one embodiment of a prosthetic foot 100. The prosthetic foot 100 can have a foot member 10 that extends from a proximal section 12 to a distal section 14 and is attached to a resilient heel member 500. In the illustrated embodiment, the proximal section 12 can be generally vertically oriented, and the distal section 12 can be generally horizontally oriented. The foot member 10 can have a curved portion (not illustrated) between the proximal section 12 and the distal section 14. The proximal section 12 can extend to a proximal end 12a and can be generally near the location of a natural human ankle. In one embodiment, the distal section 14 can extend to a distal end 14a generally at a location of natural human toes. In another embodiment, the proximal section 12 can be generally inclined with respect to the distal section 14 at an angle other than 90° (e.g., inclined at a substantially constant angle between the proximal end 12a and the distal end 14a). It should be understood, however, that the prosthetic foot can have other shapes. For example, in other embodiments, the foot member 10 can be generally planar (e.g., substantially flat) from the proximal end 12a to the distal end 14a. In another embodiment, the foot member 10 can have a curved section (e.g., c-shaped) section between the proximal section 12 and distal section 14.

In one embodiment, the foot member 10 is a plate-like member with generally planar top and bottom surfaces and generally rectangular transverse cross-sections. In some embodiments, the foot member 10 can be formed of multiple layers of material that define a monolithic piece. In some embodiments, the foot member 10 can have one or more longitudinal slots or splits that extend linearly or in a curved manner toward the front of the foot member 10. In one embodiment, the foot member 10 can have a plurality of such longitudinal splits or slots. In another embodiment, the one or more splits or slots can extend to the front edge of the foot member 10 so as to define separate toe elements.

With continued reference to FIG. 1, the prosthetic foot 100 can have an adapter 200 that attaches to the proximal section 12 of the foot member 10. The adapter 200 extends generally vertically from a proximal end 202 to a distal end 204. The adapter 200 can have a base 210 that is operably coupled to the proximal section 12 of the foot member 10. In one embodiment shown in FIG. 1, the base 210 has a cavity to receive at least a portion of the proximal section 12 of the foot member 10. In one embodiment, the base 210 is attached to the foot member 10 by sliding over the proximal end 12a of the foot member 10.

In one embodiment, an adhesive or a bonding agent (e.g., epoxy) can be applied to the proximal section 12 or the interior surfaces of the base 210 to secure the adapter 200 to the proximal section 12 of the foot member 10. For example, an adhesive can be injected into the adapter 200 via an aperture that communicates with the cavity of the base 210, so that the adhesive injected through the aperture flows into the cavity and around the proximal section 12 of the foot member 10. In one embodiment, the adapter 200 can have an aperture 206 as shown in FIG. 1. The aperture 206 can allow air to flow out of the cavity as an adhesive is injected into the adapter 200 or as the adapter 200 is fitted over the proximal section 12 of the foot member 10. In another embodiment, fasteners can be used to secure the adapter 200 to the foot member 10. A connector 205 can be disposed on the proximal end 202 of the adapter 200 for coupling the foot member 10 to a prosthetic pylon or socket. In the illustrated embodiment, the connector 205 is a male pyramid connector. However, in other embodiments, the connector 205 can be a tube clamp or other attachment device. In one embodiment, the connector 205 can be secured to the adapter 200 with adhesive or a bonding agent. The connector 205 can also be secured to the adapter 200 with fasteners or other hardware. Additionally or alternatively, the connector 205 can be threadably attached to adapter 200.

In various embodiments described below, the transverse cross-section of the foot member 10 can include a hybrid material layup having at least two different material layers. Additional prosthetic foot designs that can include the hybrid material layup embodiments disclosed herein can include the following models by Össur of Rekjavik, Iceland: Axia™, Ceterus™, Elation™, LP Ceterus™, LP Vari-Flex™, Modular III™, Re-Flex VSP®, Cheetah™, Flex-Sprint™, Flex-Run™, Talux®, Vari-Flex®, Flex-Foot® Junior, Sure-Flex, Vari-Flex XC Rotate™, LP Rotate™, LP Re-Flex VSP, Re-Flex Rotate™ Re-Flex Shock™, Flex-Foot Balance, Flex-Foot Assure, and Balance™ Foot J.

Figure 2:
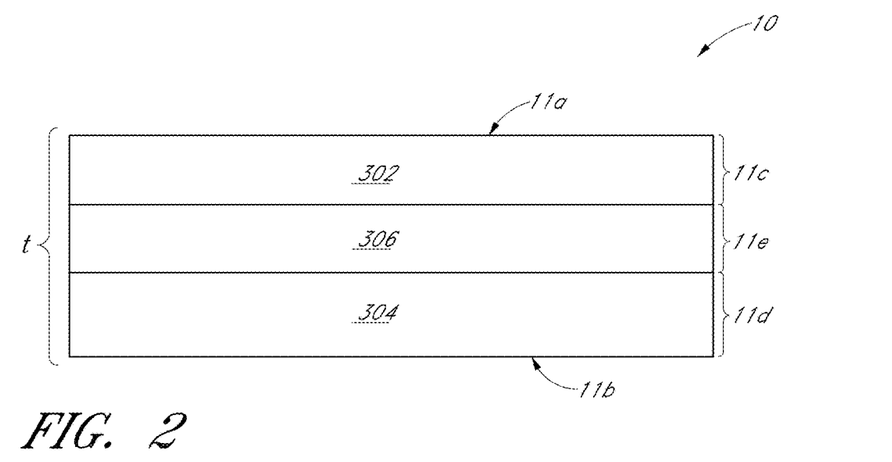
FIG. 2 is a schematic view of one embodiment of a transverse cross-section of a prosthetic foot plate with a hybrid layup arrangement.

FIG. 2 illustrates one embodiment of a cross-section of the foot member 10 generally transverse to the longitudinal axis of the prosthetic foot 100. In the illustrated embodiment, the foot member 10 can include three sections. An upper section 302, which can define an upper surface 11a of the foot member 10, can be made of one or more layers of a first material. In the illustrated embodiment, the upper section 302 has a first thickness 11c. A lower section 304, which can define a lower surface 11b of the foot member 10, can be made of one or more layers of a second material. In the illustrated embodiment, the lower section 304 has a second thickness 11d. A central or core section 306 can be disposed between the upper and lower sections 302, 304 and can be made of one or more layers of a third material. In the illustrated embodiment, the central section 306 has a third thickness 11e. In one embodiment, the upper 302, lower 304 and central 306 sections together define a thickness t of the foot member 10. It should be understood, however, that the cross-section of the foot member 10 can have fewer or more sections than discussed above. For example, in another embodiment, the foot member 10 can have two sections. In another embodiment, the foot member 10 can have four or more sections.

In one embodiment, the foot member 10 can be made of two or more sections. Each section of the foot member 10 can be made of one or more layers of a material. Each section can be made of different materials and can have a different number of layers, layer thickness and/or section thickness. The two or more sections together can provide a hybrid layup arrangement or material structure for the construct of the foot member 10. In one embodiment, the foot member 10 can be made of carbon fiber layers in combination with layers of one or more additional materials that are more flexible or "softer" than carbon fiber.

With further reference to FIG. 2, in one embodiment, the materials of the first 302 and second 304 sections (i.e. the first and second materials) can be the same, and can be different from the material of the third section 306 (i.e. the third material). In such an embodiment, the third material can have a different stiffness and/or flexural modulus from the first and second materials. In another embodiment, the first, second and third materials can be different from each other, each having a different stiffness and/or flexural modulus. In one embodiment, the thickness 11e of the core section 306 can be greater than the thickness 11c of the upper section 302 and greater than the thickness 11d of the lower section 304. In one embodiment, the third material can include carbon fiber and the first and second materials can include glass fiber. In another embodiment, the third material can include other materials, such as Basalt fiber, aramid fiber (such as Kevlar®), polyethylene fiber (Dyneema® or Spectra®), and Zylon. It should be appreciated, however, that the third material can include other types of fibers or suitable materials. In one embodiment, the first and/or second materials can include E-Glass fiber, such as woven E-Glass fiber, and/or S-Glass fiber. It should be appreciated, however, that the first and second materials can include other types of fibers or suitable materials. For example, in another embodiment, the core or central section 306 of the foot member 10 can be made of glass fiber and the upper and lower sections 302, 304 of the foot member 10 can be made of carbon fiber.

Figure 3:
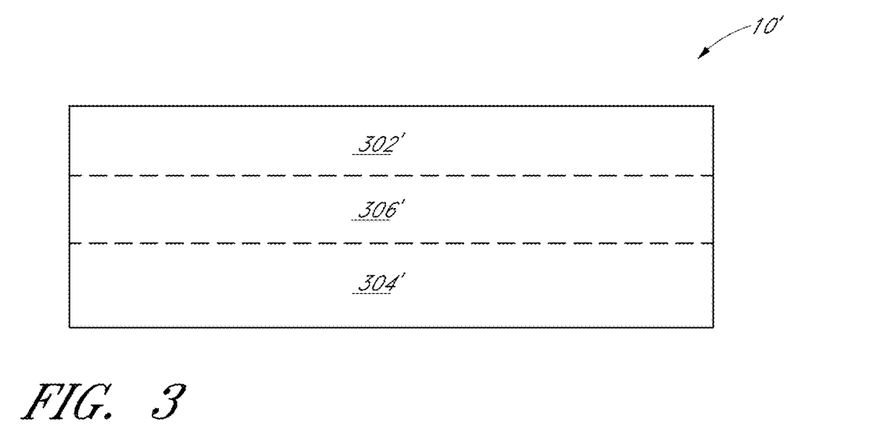
FIG. 3 is a schematic view of another embodiment of a transverse cross-section of a prosthetic foot plate with a hybrid layup arrangement.

FIG. 3 shows another embodiment of a prosthetic foot member 10', where the cross-section of the foot member 10' is defined by an upper section 302', a lower section 304' and a central section 306'. In the illustrated embodiment, the boundary between the central section 306' and the upper and lower sections 302', 304' is not a definite boundary, so that there may be layers of the third material present in the upper and lower sections 302', 304' and there may be layers of the first and second materials present in the central section 306'. In such an embodiment, the layers of the first, second and/or third materials can be intermixed within the upper, lower and central sections 302', 304', 306' of the foot member 10'.

Figure 4:
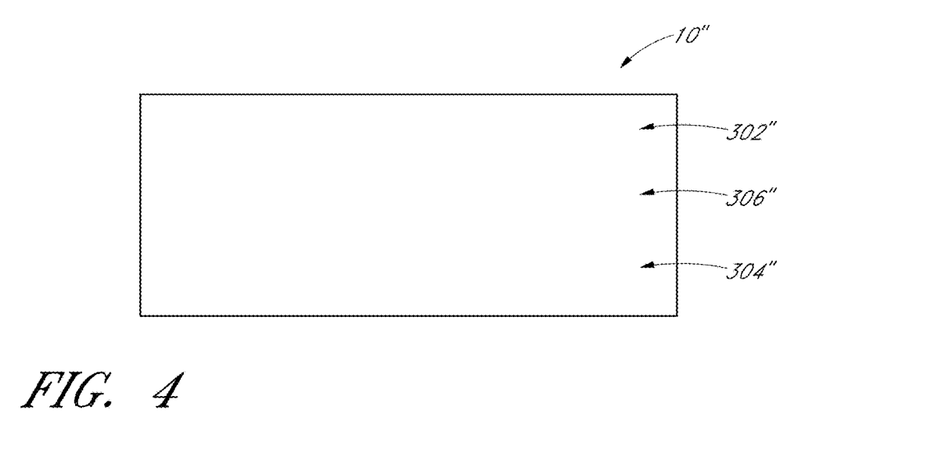
FIG. 4 is a schematic view of another embodiment of a transverse cross-section of a prosthetic foot plate with a hybrid layup arrangement.

FIG. 4 shows another embodiment of a prosthetic foot member 10", where the cross-section of the foot member 10" includes an upper, lower and central sections 302", 304", 306", but where the material layers in these three sections are intermixed so that the cross-section of the foot member 10" is substantially seamless, without boundaries between the materials of the three sections 302", 304", 306". For example, in one embodiment, the proportion of third material layers, relative to all material layers, can be greater in the central section 306" and decrease toward the top and bottom of the foot member 10", and the proportion of first and second material layers, relative to all material layers, can be greater in the upper and lower sections 302", 304" and decrease toward the center of the foot member 10".

Figure 5:
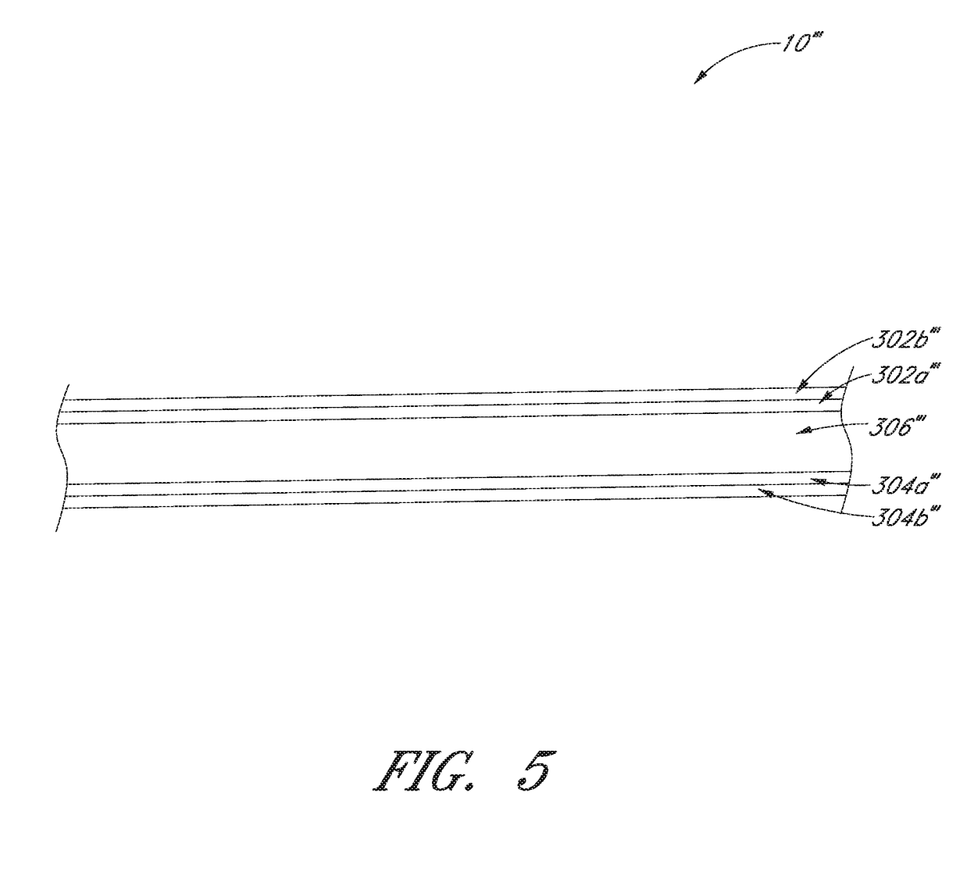
FIG. 5 is a schematic view of another embodiment of transverse cross-section of a prosthetic foot plate with a hybrid layup arrangement.

FIG. 5 shows another embodiment of a prosthetic foot member 10''', where the cross-section of the foot member 10''' has a central section 306''' of carbon fiber, and the upper and lower sections have layers of woven E-Glass 302b''', 304b''' and S-Glass 302a''', 304a'''. In the embodiment shown in FIG. 5, the layers of S-Glass 302a''', 304a''' are adjacent the central section 306''', and the layers of E-Glass 302b''', 304b''' are adjacent the layers of S-Glass 302a''', 304a'''.

In one embodiment, the two or more materials of the hybrid layup of the foot member 10, and/or the hybrid layup arrangement can be selected to provide an increased level of strength (e.g., can be 30% stronger or more) to the prosthetic foot, while generally maintaining the same flexibility or stiffness, as compared to a corresponding foot member made of only one material (e.g., carbon fiber) and having the same or similar profile (e.g., cross-sectional dimensions) as the overall hybrid layup. In another embodiment, the two or more materials of the hybrid layup of the foot member 10, and/or the hybrid layup arrangement can be selected to provide an increased level of strength as compared to a corresponding foot member made of only one material (e.g., carbon fiber) and sized to have generally the same flexibility or stiffness as the overall hybrid layup. In such an embodiment, the hybrid layup can be arranged to handle a greater load and have the same flexibility as a hypothetical single-material foot arrangement, but can have a correspondingly different and/or greater cross-sectional area and/or weight as compared to the single-material foot arrangement. In one embodiment, the overall thickness of the composite member is preferably within 50% of the hypothetical single-material plate-like foot member and more preferably within 25-40% of the hypothetical single-material plate-like foot member.

In another embodiment, the two or more materials of the hybrid layup of the foot member 10, and/or the hybrid layup arrangement can be selected to provide generally the same strength, but increased flexibility (i.e., a decreased stiffness) as compared to a corresponding foot member made of only one material (e.g., carbon fiber) and having the same or similar profile (e.g., cross-sectional dimensions) as the overall hybrid layup. In another embodiment, the two or more materials of the hybrid layup of the foot member 10, and/or the hybrid layup arrangement can be selected to provide an increased level of flexibility (i.e., a decreased stiffness) as compared to a corresponding foot member made of only one material (e.g., carbon fiber) and sized to have generally the same strength as the overall hybrid layup. In such an embodiment, the hybrid layup can be arranged to be more flexible and have the same strength as a hypothetical single-material foot arrangement, but can have a different cross-sectional area and/or weight as compared to the single material foot arrangement. In one embodiment, the overall thickness of the composite member is preferably within 10% of the hypothetical single-material plate-like foot member.

Table 1, below, shows a comparison of the material properties of examples of carbon fiber and S-glass fiber. The Table shows that S-glass material has a lower flexural strength (i.e., it is softer), but has higher elongation at failure than carbon fiber.

TABLE 1

Comparison of Carbon fiber and S-glass fiber

| Material | E<br>Young's modulus,<br>flexural (GPa) | $\sigma_{max}$<br>Flexural strength<br>(MPa) | Elongation<br>at failure |
|---|---|---|---|
| Carbon fiber uni | 125 | 1930 | ~2 |
| S-glass uni | ~50 | ~1460 | >3.3% |

In another embodiment, the hybrid layup arrangement of the two or more materials can be chosen to provide increased strength of the foot member 10, while providing similar stiffness as a foot member made of only carbon fiber layers. For example, the proportion of the two or more materials in the hybrid layup of the foot member 10 can be selected to provide increased strength as compared to a single-material carbon fiber prosthetic foot sized to have generally the same stiffness as the hybrid layup. In such an embodiment, the hybrid layup can have a correspondingly different and/or greater cross-sectional area and/or weight as compared to the single-material carbon fiber prosthetic foot sized to have generally the same stiffness as the hybrid layup. In such an embodiment, the proportional increase in strength of the hybrid layup can be greater than the corresponding proportional increase in cross-sectional area and/or weight of the hybrid layup. In other words, the cross-sectional area and/or weight of the hybrid layup is greater than an equivalent single-material carbon fiber prosthetic foot sized to have the same stiffness as the hybrid layup, but is less than an equivalent single-material carbon fiber prosthetic foot sized to have the same strength as the hybrid layup.

In another embodiment, the hybrid layup arrangement of the two or more materials can be chosen to provide increased flexibility (i.e., a decreased stiffness) of the foot member 10, while providing similar strength as a foot member made of only carbon fiber layers. For example, the proportion of the two or more materials in the hybrid layup of the foot member 10 can be selected to provide increased flexibility (i.e., a decreased stiffness) as compared to a single-material carbon fiber prosthetic foot sized to have generally the same strength as the hybrid layup. In such an embodiment, the hybrid layup can have a different cross-sectional area and/or weight as compared to the single-material carbon fiber prosthetic foot sized to have generally the same strength as the hybrid layup.

In one embodiment, for a given set of materials in the hybrid layup, an idealized ratio of the cross sectional area (e.g. thickness/height and/or width) of each section can be determined such that under an applied load provided to the hybrid layup, the ratio of maximum stress of a given section over the flexural strength of that given section is approximately equal for all sections of the hybrid layup, wherein the maximum stress of a given section is the maximum stress experienced by that section under the applied load provided to the hybrid layup. In one embodiment, the idealized ratio can allow the material sections achieve substantially simultaneous failure when the composite member is subjected to a bending force greater than a flexural breaking force of the plate-like foot member. In one embodiment, analytical calculations, such as the modified section method for composite beams, can be used to calculate the maximum stress and moment of inertia of the sections in order to determine the idealized ratio. The analytical calculations can be used for composite beams of regular cross-section, irregular cross section, sandwich beams, non-sandwich beams, as well as any number of materials or layers. In another embodiment, numerical techniques, such as the finite element method, can be used to calculate the maximum stress and moment of inertia of the sections in order to determine the idealized ratio. In another embodiment, experimental methods, such as the three-point or four-point bending test, can be used to determine the idealized ratio.

In one embodiment the hybrid layup can be provided with at least a first section and a second section provided on top of one another. The first section is substantially defined by one or more layers having a first fiber material and the second section is substantially defined by one or more layers having a second fiber material. The sections together define a composite member and further define the total thickness of the plate-like elongate foot member. The thickness of each section relative to the total thickness of the composite member can be configured such that the ratio of maximum stress of a given section over the flexural strength of that given section is approximately equal for all sections, wherein the maximum stress of a given section is the maximum stress experienced by that section under an applied load provided to the composite member. In an embodiment, the ratios of maximum stress over the flexural strength of the sections are preferably within 20% of each other when the foot member has two sections and the ratios of maximum stress over the flexural strength of all sections are preferably within 5% of each other when the foot member has three or more sections. As described above, the ratios of the maximum stress over the flexural strength of the sections can be calculated analytically, for example using the modified section method for composite beams. The ratios can additionally or alternatively be calculated numerically, using a numerical method such as the finite element method or the finite difference method. The ratios can additionally or alternatively be calculated experimentally using physical testing of specimens. When the ratios are determined experimentally, the preferred testing method is the three-point bending test and/or the four-point bending test using ASTM D790-10, "Standard Test Methods for Flexural Properties of Unreinforced and Reinforced Plastics and Electrical Insulating Materials," and ASTM D6272-10, "Standard Test Method for Flexural Properties of Unreinforced and Reinforced Plastics and Electrical Insulating Materials by Four-Point Bending," respectively. It should be appreciated that the ratios can be determined by a combination of analytical, numerical, and/or experimental methods.

In one embodiment, the stiffness of the sections of the hybrid layup can be different. In the case of a two section composite, the upper section can have either a greater or lower stiffness than the lower section. In the case of a composite with three or more sections, the core section can have either a greater or lower stiffness than the upper and lower sections and the upper and lower sections can additionally have the same stiffness or a different stiffness from each other. It should be appreciated that some or all of the sections can have the same thickness or differing thicknesses. In one embodiment, a three section composite can be provided with a core section and an upper and lower section, where the upper and lower sections can have the same thickness and can optionally be made of the same material.

In an embodiment, a two section hybrid layup is provided where the bottom section is made of carbon fiber layers and the top section is made of glass fiber layers. In an embodiment, a two section hybrid layup is provided where the bottom section is made of glass fiber layers and the top section is made of carbon fiber layers. In an embodiment, a three section hybrid layup is provided where a core section is made of carbon fiber layers and upper and lower sections are made of glass fiber layers. In an embodiment, a three section hybrid layup is provided where a core section is made of glass fiber layers and upper and lower sections are made of carbon fiber layers.

In an embodiment, a three section hybrid layup is provided with a core section, an upper section and a lower section, wherein the upper, lower and core sections together define a total thickness of the plate-like elongate foot member. In one embodiment, the core section is configured to fail when the plate-like member is subjected to a bending force greater than a flexural breaking force of the plate-like foot member. In such an embodiment, the core section is configured to break and the upper and lower sections are configured to remain intact and contain the broken core section to maintain the plate-like foot member as one piece. In one embodiment, the upper and lower sections are configured to fail, but remain intact, when the plate-like member is subjected to a bending force greater than a flexural breaking force of the plate-like foot member so as to maintain the plate-like foot member as one piece. In an alternative embodiment, the upper and lower sections are configured not to fail and remain intact to maintain the plate-like foot member as one piece.

Table 2, below, shows different layup configurations for a prosthetic foot member and the different proportions in which materials in a hybrid layup arrangement are provided. For example, in a prosthetic foot member having a hybrid layup arrangement of glass-carbon-glass (e.g., where the central section 306 of the foot member is made of carbon fiber layers and the upper and lower sections 302, 304 of the foot member are made of glass fiber layers), the proportion of the materials in the foot member can be 56% carbon fiber and 44% glass fiber, with the carbon fiber section being disposed between two glass fiber sections, each glass fiber section having a proportion of 22% of the overall hybrid layup.

TABLE 2

Comparison of Different Hybrid Layup Arrangements

| Layup Configuration of Foot Member | Ideal ratio (best case scenario) of different materials in Layup | Performance |
| --- | --- | --- |
| Carbon | N/A | N/A |
| Carbon Glass | (0.61/0.39) | Stronger than pure carbon at the cost of increased weight and thickness for the same stiffness |

TABLE 2-continued

Comparison of Different Hybrid Layup Arrangements

| Layup Configuration of Foot Member | Ideal ratio (best case scenario) of different materials in Layup | Performance |
| --- | --- | --- |
| Glass Carbon | (0.39/0.61) | Use carbon-glass variation instead |
| Glass Carbon Glass | 0.22/0.56/0.22 | Stronger than pure carbon at the cost of increased weight and thickness for the same stiffness |
| Carbon Glass Carbon | N/A | N/A |
| Glass | N/A | Stronger than pure carbon at the cost of increased weight and thickness for the same stiffness |

The foot member 10 with the hybrid layup arrangement can have a different failure performance than a similarly dimensioned foot member having a carbon fiber layup arrangement. In one embodiment, the foot member with the hybrid layup arrangement, such as a foot member 10 made of a core section of carbon fiber layers and upper and lower sections made of glass fiber layers as depicted in FIG. 2, will fail by delaminating. In such a configuration, the carbon core or central section 306 will break but the outer glass fiber sections will generally hold the foot in one piece. In contrast, a foot member made of carbon fiber alone will fail by breaking into pieces.

Figure 6:
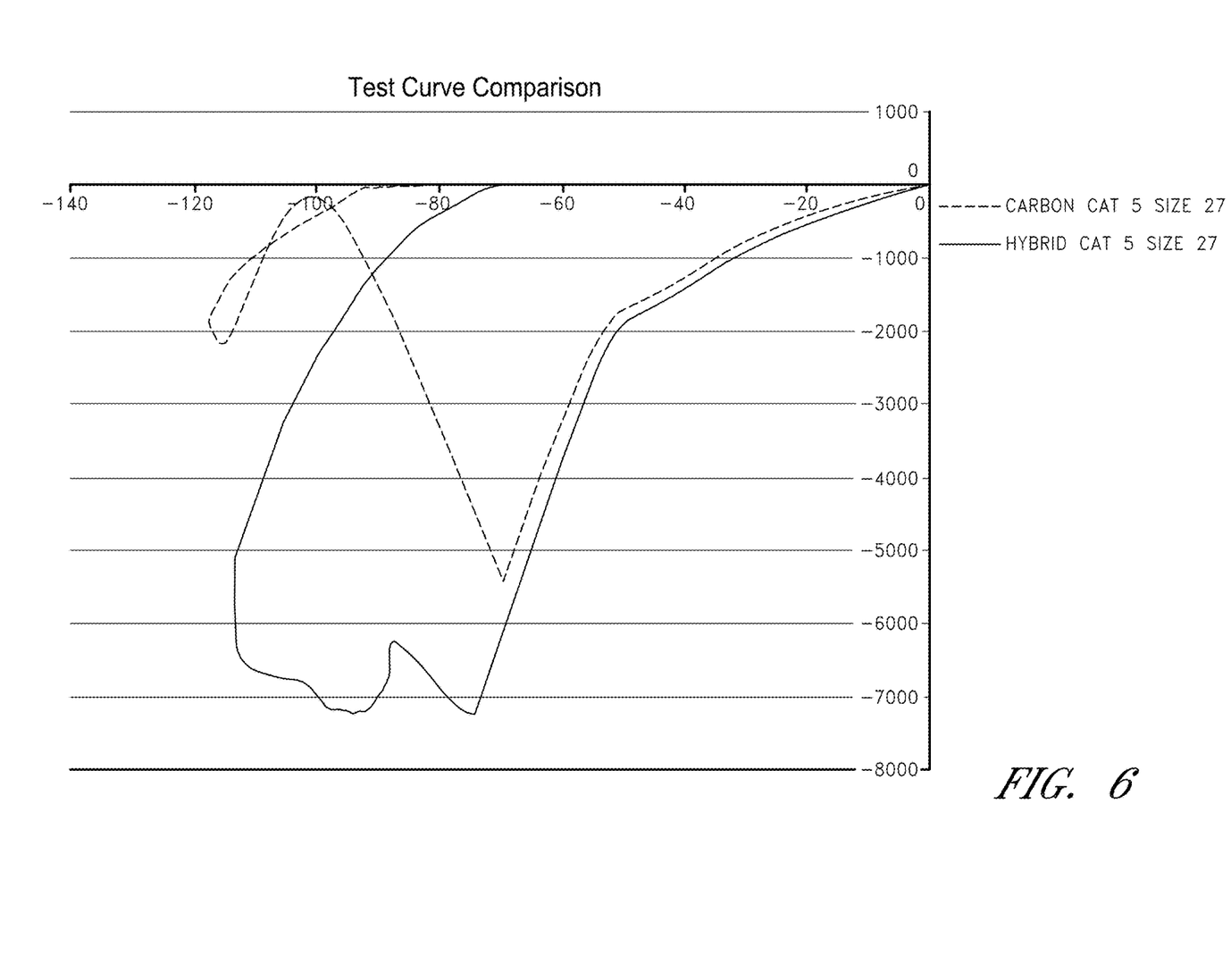
FIG. 6 is a graph showing a comparison in strength and stiffness of a carbon fiber prosthetic foot and a prosthetic foot having a hybrid material layup.

FIG. 6 shows a graph of force (in Newtons) as a function of deflection (in mm) for two different prosthetic feet. One prosthetic foot has a single-material carbon fiber layup structure and the second prosthetic foot has a hybrid layup structure with carbon fiber layers and glass fiber layers. As shown in FIG. 6, the prosthetic foot member with the carbon fiber layup broke and/or failed at approximately 5300 N, whereas the prosthetic foot member with the hybrid layup broke and/or failed at approximately 7100 N. Accordingly, the prosthetic foot member with the hybrid layup structure was stronger than the prosthetic foot member with the single-material carbon fiber layup structure.

Figure 7:
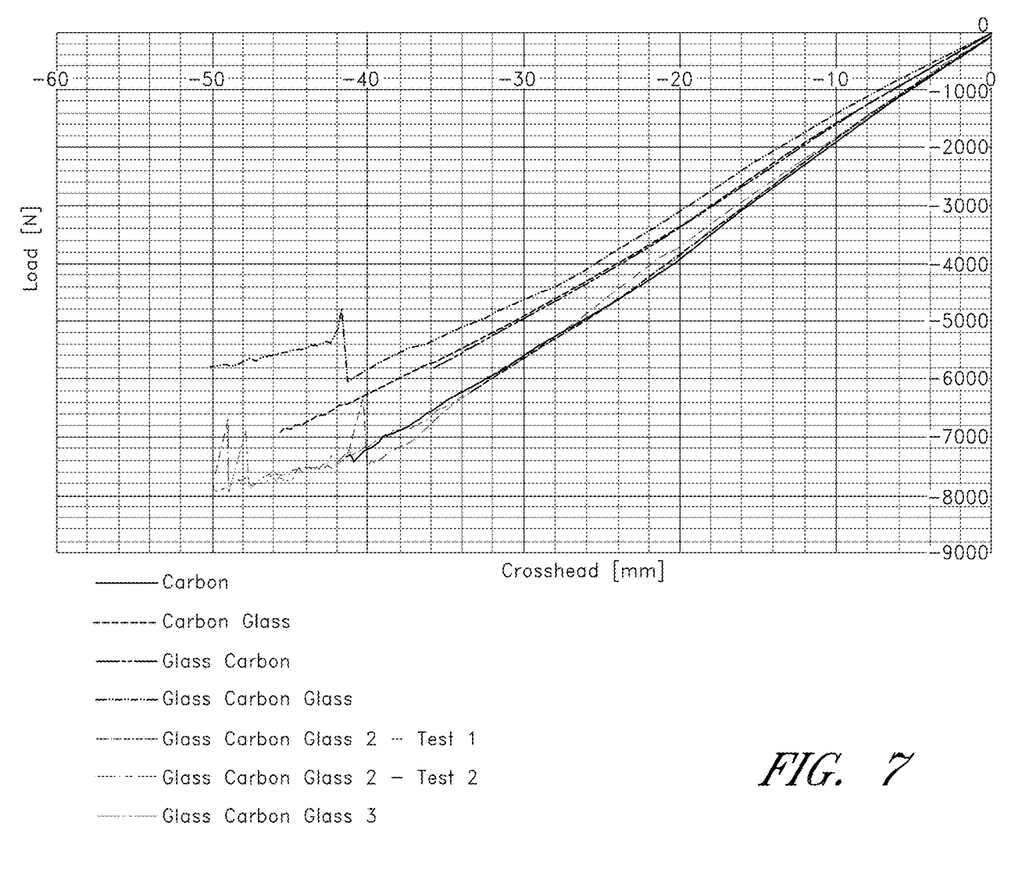
FIG. 7 is a graph showing a comparison in strength and stiffness of a carbon fiber flat plate and various different flat plates having a hybrid material layup using a 3-point bending test.

Table 3, below, shows test results of various layup arrangements for a flat plate member or composite beam using a 3-point bending test as per ASTM D790-10, "Standard Test Methods for Flexural Properties of Unreinforced and Reinforced Plastics and Electrical Insulating Materials," as compared to a flat plate member made of a single-material carbon fiber layup. The objective of these tests is to experimentally determine which types of hybrid plate configurations can handle the greatest loads. During testing, the top of the plate member was in compression and the bottom of the plate member was in tension. The span in the bending test was 240 mm and the plates were approximately 8.5 mm wide. Uni layers were 0.15 mm thick while cloth layers were 0.25 mm. FIG. 7 shows a graph of force or load (in Newtons) as a function of deflection (in mm), illustrating the performance of the different layup arrangements described in Table 3. As shown in FIG. 7, the flat plate member or composite beam with the glass-carbon-glass hybrid layup arrangement exhibited a higher strength than the rest of the layup arrangements, including the flat plate member made of only carbon fiber.

TABLE 3

Test Results of Various Layup Arrangements for a Composite Beam

| Layup configuration (from the top to the bottom) | Thickness of uni layers (mm, in order of materials from top to bottom) | Type of cloth (3 layers on each side in every plate) | Performance |
|---|---|---|---|
| Carbon | 3.75 | Carbon, 45° | Reference plate |
| Carbon Glass | 1.8, 2.7 | Carbon, 45° | Much stronger than glass carbon, despite theory stating they should be the same. Carbon part failed + cloth. Ratio = 0.39/0.61 |
| Glass Carbon | 2.7, 1.8 | Carbon, 45° | Much weaker than carbon glass, despite theory stating they should be the same. Carbon part failed + cloth. Ratio = 0.61/0.39 |
| Glass Carbon Glass | 1.05, 2.4, 1.05 | Carbon, 45° | Only the carbon cloth cracked, which was enough to weaken the plate considerably. Switched to glass cloth for next attempts. Ratio = 0.2/0.6/0.2 |
| Glass Carbon Glass 2 | 1.05, 2.7, 1.05 | Glass, 0° | First attempt at breaking it failed (not enough deflection), resulting in inconclusive results on second attempt. Most likely scenario was that the glass cloth cracked during the first test. Carbon core + glass cloth failed eventually. Ratio = 0.21875/0.5625/0.21875 |
| Glass Carbon Glass 3 | 1.05, 2.7, 1.05 | Glass, 0° | Very similar results to the previous plate, should have taken much higher loads according to theory but was still higher than pure carbon. Carbon core + glass cloth failed. Ratio = 0.21875/0.5625/0.21875 |

Although the invention is described above with respect to prosthetic feet, the invention can be used with other parts of the body, including, for example, in a full-leg prosthesis wherein the composite plate member can form part of a thigh or knee region.

In some embodiments, the embodiments disclosed above can be used in a method of designing a prosthetic foot. For example, in one embodiment, a method of designing a prosthetic foot can include determining a hybrid layup arrangement having at least two different material layers, in the manner described above, to provide a prosthetic foot member having generally the same strength as a similarly sized foot member made of only one material (e.g., carbon fiber), but having greater flexibility than said foot member made of only the one material. In another embodiment, a method of designing a prosthetic foot can include determining a hybrid layup arrangement having at least two different material layers, in the manner described above, to provide a prosthetic foot member having increased flexibility as compared to a corresponding foot member made of only one material (e.g., carbon fiber) and sized to have generally the same strength as the overall hybrid layup. In another embodiment, a method of designing a prosthetic foot can include determining a hybrid layup arrangement having at least two different material layers, in the manner described above, to provide a prosthetic foot member having generally the same stiffness as a similarly sized foot member made of only one material (e.g., carbon fiber), but having greater strength than said foot member made of only the one material. In another embodiment, a method of designing a prosthetic foot can include determining a hybrid layup arrangement having at least two different material layers, in the manner described above, to provide a prosthetic foot member having generally an increased level of strength as compared to a corresponding foot member made of only one material (e.g., carbon fiber) and sized to have generally the same flexibility as the overall hybrid layup.

Of course, the foregoing description is that of certain features, aspects and advantages of the present invention, to which various changes and modifications can be made without departing from the spirit and scope of the present invention. Moreover, the foot member need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of the specific features and aspects between and among the different embodiments may be made and still fall within the scope of the invention. Accordingly, it should be understood that various features and aspects of the disclosed embodiments can be combined with or substituted for one another in order to form varying modes of the discussed foot member with the hybrid layup arrangement.

What is claimed is:

1. A method of making a prosthetic foot comprising a hybrid layup having at least a first section and a second section provided on top of one another, wherein the first section comprises a plurality of first layers comprising a first fiber material and the second section comprises a plurality of second layers comprising a second fiber material that is different from the first fiber material, the method comprising:
   determining desired thicknesses of the first section and the second section to provide for simultaneous breakage of the first and second sections in the hybrid layup under an applied load provided to the hybrid layup, wherein the applied load is provided to the hybrid layup at the same location along a length of the prosthetic foot, wherein the desired thicknesses are determined by satisfying the following:
   a first ratio, defined as a first maximum stress of the first section over a first flexural strength of the first section, is equal to a second ratio, defined as a second maximum stress of the second section over a second flexural strength of the second section, wherein the maximum stress of a given section is the maximum stress experienced by that section under the applied load;
   laying up the plurality of first layers comprising the first fiber material to form the first section of the prosthetic foot, wherein the first section is laid up to have a thickness based on the determined desired thickness for the first section; and
   laying up the plurality of second layers comprising the second fiber material to form the second section of the prosthetic foot on top of the first section, wherein the second section is laid up to have a thickness based on the determined desired thickness for the second section.

2. The method of claim 1, further comprising determining a desired thickness of a third section of the prosthetic foot provided on top of the second section, the third section comprising a plurality of third layers comprising a third fiber material, to provide for simultaneous breakage of the first, second and third sections in the hybrid layup under the applied load, wherein the thickness of the third section is determined by satisfying the following:

the first ratio, the second ratio, and a third ratio, defined as a third maximum stress of the third section over a third flexural strength of the third section, are equal; and laying up the plurality of third layers comprising the third fiber material to form the third section of the prosthetic foot on top of the second section, wherein the third section is laid up to have a thickness based on the determined desired thickness for the third section.

3. The method of claim 2, wherein the third fiber material is the same as either the first fiber material or the second fiber material.

4. The method of claim 1, wherein the first fiber material is glass fiber and the second fiber material is carbon fiber.

5. The method of claim 2, wherein the first fiber material is glass fiber, the second fiber material is carbon fiber, and the third fiber material is glass fiber.

6. A method of making a prosthetic foot comprising a first fiber material and a second fiber material that is different from the first fiber material, the method comprising:

laying up one or more first layers comprising the first fiber material to form a first section of the prosthetic foot, wherein the first section defines a first thickness; and laying up one or more second layers comprising the second fiber material to form a second section of the prosthetic foot on top of the first section, wherein the second section defines a second thickness, wherein the first and second thicknesses are selected such that under an applied load to the prosthetic foot:

$$\frac{\sigma_{1st,applied}}{\sigma_{1st,allowable}} \approx \frac{\sigma_{2nd,applied}}{\sigma_{2nd,allowable}},$$

wherein $\sigma_{1st,applied}$ is a first applied stress to the first section due to the applied load, wherein $\sigma_{1st,allowable}$ is a first stress at which the first section will break, wherein $\sigma_{2nd,applied}$ is a second applied stress to the second section due to the applied load, and wherein $\sigma_{2nd,allowable}$ is a second stress at which the second section will break.

7. The method of claim 6, wherein laying up one or more second layers comprises laying up an initial second layer directly on top of the first section.

8. The method of claim 6, wherein the first ratio is within 20% of the second ratio.

9. The method of claim 6, wherein the first ratio is within 10% of the second ratio.

10. The method of claim 6, wherein the first ratio is within 5% of the second ratio.

11. The method of claim 6, wherein the first fiber material comprises carbon fiber and the second fiber material comprises glass fiber.

12. The method of claim 6, wherein the first fiber material comprises glass fiber and the second fiber material comprises carbon fiber.

13. The method of claim 6, wherein the first thickness is greater than the second thickness.

14. The method of claim 6, wherein the first thickness is less than the second thickness.

15. The method of claim 6, further comprising:

laying up one or more third layers comprising a third fiber material to form a third section of the prosthetic foot on top of the second section, wherein the third section defines a third thickness, wherein the first, second and third thicknesses are selected such that a third ratio of an applied stress to an allowable stress of the third section is approximately equal to the first and second ratios, wherein the applied stress of the third section is due to the load applied to the prosthetic foot.

16. The method of claim 15, wherein laying up one or more third layers comprises laying up an initial third layer directly on top of the second section.

17. The method of claim 15, wherein the third thickness is approximately equal to the first thickness.

18. The method of claim 15, wherein the first and third fiber materials comprise carbon fiber and the second fiber material comprises glass fiber.

19. The method of claim 15, wherein the first and third fiber materials comprise glass fiber and the second fiber material comprises carbon fiber.

* * * * *